United States Patent [19]
Cleary et al.

[11] Patent Number: 5,186,939
[45] Date of Patent: Feb. 16, 1993

[54] LAMINATED COMPOSITE FOR TRANSDERMAL ADMINISTRATION OF FENTANYL

[75] Inventors: Gary W. Cleary, San Mateo; Samir D. Roy, Redwood City, both of Calif.

[73] Assignee: Cygnus Therapeutic Systems, Redwood City, Calif.

[21] Appl. No.: 823,017

[22] Filed: Jan. 15, 1992

[51] Int. Cl.$^5$ ............................................. A61F 13/02
[52] U.S. Cl. ................................. 424/448; 424/449; 424/444
[58] Field of Search .......................... 424/448, 449

[56] References Cited

U.S. PATENT DOCUMENTS 4,568,343 2/1986 Leeps et al. .................. 424/449
4,588,580 5/1986 Gals et al. .................... 424/449

Primary Examiner—Thurman K. Page
Assistant Examiner—Leon R. Horne
Attorney, Agent, or Firm—Morrison & Foerster

[57] ABSTRACT

A laminated composite for administering fentanyl transdermally that consists of a fentanyl-impermeable occlusive backing layer and an adhesive fentanyl reservoir layer comprising fentanyl dissolved in an amine-resistant polydimethylsiloxane that has a high diffusivity and poor solubility for fentanyl which enables the fentanyl to be released rapidly from the composite over a one day period with little residual fentanyl left in the reservoir thereafter.

8 Claims, 1 Drawing Sheet

LAMINATED COMPOSITE FOR TRANSDERMAL ADMINISTRATION OF FENTANYL

This application is a continuation of Ser. No. 700,563 filed May 15, 1991 which is a continuation of application Ser. No. 588,702 now abandoned filed Sep. 27, 1990 which is a continuation of application Ser. No. 07/425,041 filed Oct. 20, 1989, now abandoned, which is a continuation-in-part of application Ser. No. 211,337 filed Jun. 24, 1988, now abandoned, with is a continuation-in-part of application Ser. No. 179,423 filed Apr. 8, 1988 now U.S. Pat. No. 4,906,463, which is a continuation-in-part of Ser. No. 07/079,801 filed Jul. 30, 1987, now abandoned, which is a continuation-in-part of application Ser. No. 07/041,793, filed Apr. 23, 1987, now abandoned.

DESCRIPTION Technical Field

This invention is in the field of devices for administering fentanyl transdermally for the relief of postoperative and chronic cancer pain. More particularly it relates to a laminated composite for administering fentanyl transdermally for approximately one day after which time a substantial amount of the fentanyl in the device has been depleted therefrom.

BACKGROUND

Fentanyl, a synthetic opiate with a potency of 50 to 100 times that of morphine, is used clinically for the relief of pain in postsurgical patients as well as in terminal cancer patients. Pharmacodynamic studies after intramuscular administration of fentanyl have indicated that the peak analgesic effects generally occur at 1 hour after intravenous administration and are sustained for a shorter duration than morphine. The mean effective analgetic plasma concentrations of fentanyl are about 1 and 3 ng/ml for postoperative and intraoperative administration, respectively, although there is considerable intersubject variation. Up to 10 ng/ml plasma concentration of fentanyl yields similar analgetic effects in terminal cancer pain. The development of tolerance and physical dependence with repeated use of fentanyl is similar to that of other opioid drugs. However, lower initial dose may reduce the tolerance level of fentanyl.

The decline over time in fentanyl plasma concentration after intravenous administration appears to be triexponential with initial distribution phase followed by two elimination phases. The volume of distribution ranged from 4.4 to 59.7 liters, the terminal elimination half-life ranged from 141 to 853 minutes while total body clearance values ranged from 160 to 1530 ml/minute. The plasma protein binding in humans is reported to be 85%. Fentanyl is cleared primarily by metabolic routes in healthy volunteers and surgical patients, with renal clearance of fentanyl accounting for only 6% of the dose in volunteers.

Fentanyl (the citrate salt) is most frequently given intravenously or intramuscularly to achieve therapeutic effects. Fentanyl citrate is preferred for injection because of its aqueous solubility. Absorption of this compound via other routes is limited.

Conventional ways of delivering fentanyl have some major drawbacks. Although intravenous or intramuscular administration of fentanyl produces significant analgesic effects, it has to be given with excessive frequency because of high metabolic clearance. Oral absorption is variable and incomplete due to first-pass metabolism. Fentanyl also tends to cause respiratory depression in pain-relieving doses when administered intravenously.

Delivering fentanyl transdermally can minimize many of these problems, including the tendency for fentanyl underutilization by the physician. Side-effects which derive from the pulsed nature of delivery of parenteral dosage forms of fentanyl can be offset. In other words, the peak-and-valley of blood levels associated with discrete doses of drug can be eliminated. Moreover, the steady state plasma level of fentanyl can be maintained over the longer period of time by a constant flux of this drug through skin. Steady state plasma and tissue concentrations of fentanyl provide less toxicity risks than peak-and-valley concentrations resulting from injections.

European Patent No. 0171742 and U.S. Pat. No. 4,626,539 describe transdermal delivery of opioids and the use of various vehicles to enhance the penetration of opioids through skin. U.S. Pat. No. 4,588,580 describes specific systems for administering fentanyl. The particular device described in the patent uses ethanol as an enhancer and the fentanyl-ethanol mixture is contained in the reservoir in a fluid form. Using such a form complicates the procedure for manufacturing the device. Further, ethanol enhances the skin flux of fentanyl 3-4 fold as compared to fentanyl flux from water. That level of enhancement may not be sufficient to deliver an adequate amount of fentanyl transdermally through a reasonably-sized system because of high volume of distribution of fentanyl in the body. Also, the amount of fentanyl residing in the patented system at the completion of the prescribed wearing time is substantial. Since fentanyl is a restricted drug, significant amounts of residual fentanyl pose regulatory (DEA) problems and potential safety risks.

DISCLOSURE OF THE INVENTION

The invention is a solid-state laminated composite for administering fentanyl transdermally comprising:
(a) a backing layer that is substantially impermeable to fentanyl and defines the face surface of the composite,
(b) an adhesive-drug reservoir layer that defines the basal surface of the composite during use and comprises:
 (i) 1 to 5% by weight fentanyl;
 (ii) 1 to 10% by weight propylene glycol monolaurate (PGML);
 (iii) 85 to 98% by weight of an amine resistant pressure sensitive adhesive polymer having a diffusivity to fentanyl in the range of $10^{-8}$ to $10^{-11}$ cm$^2$/sec and a solubility for fentanyl in the range of 1.5 to 5 mg/ml, said composite exhibiting a steady state fentanyl skin flux in the range of about 2 to about 10 mcg/cm$^2$/hr and administering at least about 75% of the fentanyl in the composite during approximately the first day of use.

Prior to use the composite includes a release liner layer that covers said basal surface of the adhesive-drug reservoir layer and is adapted to be removed from the device to expose said basal surface and permit the composite to be adhered to the skin.

BRIEF DESCRIPTION OF THE DRAWINGS

Like elements are referred to by like reference numerals in the drawings.

MODES FOR CARRYING OUT THE INVENTION

Figure 1:
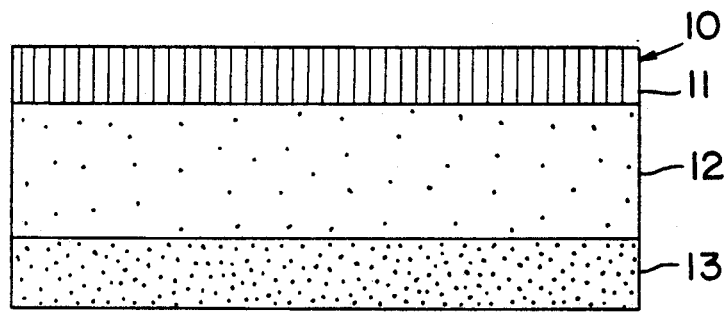
FIG. 1 is a sectional view of one embodiment of the invention.

FIG. 1 shows a laminated composite, generally designated 10, which is an embodiment of the invention and is designed for administering fentanyl or a fentanyl analog (for convenience the term "fentanyl" is used herein to designate both the base and analogs unless the base or analog is specified) transdermally at therapeutically effective rates. Device 10 (FIG. 1) is in the form of a three-layer laminated composite that is adapted to be adhered to a predetermined area of unbroken skin. The three layers of the device are: a first layer 11 that forms the upper face surface of the device; a fentanyl reservoir layer 12 which also acts as a pressure sensitive adhesive; and a release liner layer 13.

Figure 2:
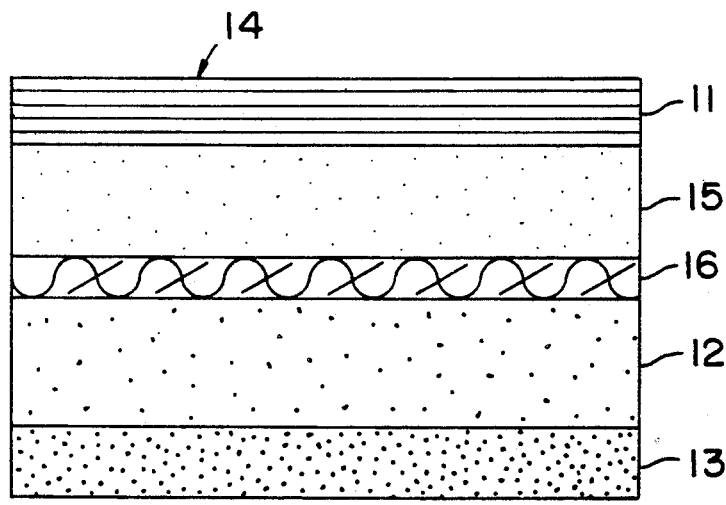
FIG. 2 is a sectional view of a second embodiment of the invention.

FIG. 2 depicts a five-layer laminated composite generally designated 14, which includes the three layers of the composite of FIG. 1 and two additional layers: an adhesive layer 15 and a structural nonwoven fabric layer 16. Layer 16 is used to provide additional firmness to the composite and layer 15 is used to adhere layer 16 to layer 11.

Layer 11 is a structural layer that provides the composite with firmness and acts as a backing. Layer 11 may be made of an occlusive (substantially water impermeable) or nonocclusive (water permeable) material. Preferably it is made of an occlusive material that is also substantially impermeable to fentanyl so that little, if any, fentanyl diffuses into layer 11 from the reservoir layer. Layer 11 will typically be in the range of 25 to 75 microns thick. Examples of materials from which layer 11 may be made are polyesters, polypropylene or polyethylene.

Layer 12 provides the reservoir for the drug. The matrix (continuous phase) of the layer is a polymer composition that has a high diffusivity for fentanyl (above about $10^{-8}$, typically $10^{-8}$ to $10^{-11}$, and preferably $10^{-8}$ to $10^{-10}$ cm$^2$/sec) and is a poor solvent for fentanyl (the solubility of fentanyl in the polymer is typically in the range of 1.5 to 5 mg/ml, preferably 1.5 to 2.5 mg/ml). This combination permits the fentanyl to be rapidly released from the composite over a short period of time (on the order of about 1 day) with little residual left in the composite thereafter.

The amount of fentanyl in the reservoir layer will usually be in the range of 0.15 to 0.5 mg/cm$^2$, preferably 0.17 to 0.3 mg, and will typically constitute 1.5 to 5% by weight, preferably 1.7 to 3% by weight, of the reservoir layer. The layer also serves as a reservoir for the permeation enhancer, PGML. Commercial PGML contains substantial amounts, i.e., up to 40% by weight, of the dilaurate (PGDL) and may also contain minor amounts e.g., up to 10% to 15% by weight) of other ingredients, such as methyl laurate or propylene glycol. Thus, as used herein, the term "PGML" intends such commercial PGML as well as more pure forms of the material. The amount of PGML in the layer will usually be in the range of 0.1 to 10 mg/cm$^2$, preferably 0.15 to 0.5 mg/cm$^2$, and will normally constitute 1 to 10% by weight, preferably 1.5 to 5% by weight of the layer. The layer also serves as the means for adhering the composite to the skin. The matrix material, therefore, must have adhesive properties and should not chemically interact with fentanyl (i.e., it must be amine-resistant) or PGML. A preferred matrix material having the above-described properties is polydimethylsiloxane admixed with 1 to 5% by weight silicone oil. The matrix will normally constitute 85 to 98% by weight, preferably 90 to 96% by weight, of the reservoir layer. The basal surface area of the composite (defined by layer 12) will usually be in the range of 5 to 50 cm$^2$, preferably 10 to 40 cm$^2$.

Layer 13 serves as a release liner that is stripped from the composite just prior to use to expose layer 12. It is made from a polymer that is substantially impermeable to fentanyl and PGML and is inherently strippable or rendered so by techniques such as silicone or fluorocarbon treatment.

The purpose of layer 16 of the composite of FIG. 2 is to provide a site for depositing fentanyl in one method of manufacturing the composite and/or when the backing layer is thin and flexible to add firmness to the composite so as to prevent the backing layer from curling. It is preferably made of a porous material such as nonwoven fabric made of polymers such as nylon or polyester. Layer 15 is an adhesive layer that serves as a means for adhering the backing layer to structural layer 16. It is preferably made of the material that forms the matrix of layer 12. In such embodiments the fentanyl and PGML will diffuse from layer 12 into layer 15 until equilibrium is reached. In this regard, layer 16, because of its porosity, offers no barrier to diffusion of fentanyl and PGML either to or from layer 15. Thus, in operation, layers 12 and 15 function as a single fentanyl/PGML reservoir matrix.

The steady state flux of fentanyl from the invention composite (measured by the test described in J. Pharm. Sci. (1983) 72:968) is in the range of 1 to 15 mcg/cm$^2$/hr, preferably 2 to 10 mcg/cm$^2$/hr, over the first one day of use. After that time the residual fentanyl in the composite should be less than about 25% and preferably less than about 15% by weight of the total fentanyl in the composite at the time of manufacture. This latter aspect of the composite is highly advantageous as fentanyl is a restricted drug and substantial exhaustion of fentanyl from the composite facilitates compliance with drug enforcement regulations.

The invention is further illustrated by the following examples. These examples are not intended to limit the invention in any manner.

EXAMPLE 1

An adhesive backing containing 2.0% silicone oil (100 centstokes, Dow Corning Medical Fluid) and 92.5% amine resistant polydimethylsiloxane (Dow Corning X7-2900) dissolved in trichlorotrifluoroethane (freon) to provide a 35% solution was prepared. The adhesive was then laminated onto a film consisting of 25 micron thick polyester film (3M, MSX-630) such that the polyester film would provide the outer backing-subassembly (L1).

A fentanyl-containing pressure-sensitive adhesive composition was prepared consisting of 1.8% fentanyl base, 4% PGML, 2.0% silicone oil (100 centstokes, Dow Corning Medical Fluid) and 92.5% amine resistant polydimethylsiloxane (Dow Corning X7-2900) dissolved in trichlorotrifluoroethane (freon) to provide a 50% solution. The drug-containing pressure-sensitive adhesive composition was cast using a 150 micron gap Gardner wet film applicator onto a fluorocarbon-coated polyester film (3M, 1022) and the solvent was evaporated to provide a 75 micron thick contact adhesive layer. A porous layer consisting of 25 micron thick Cerex film (a nylon spun-bonded nonwoven fabric obtained from James River Corp.), was laminated onto the other side of the film of drug-containing pressure-sensitive adhesive composition to form a second subassembly (L2).

The Cerex film surface of L2 was laminated to the adhesive side of L1 to provide the final five-layer laminated composite with the fluorocarbon-coated polyester film serving as a peelable release strip for the final laminate. The laminated system was allowed to equilibrate for a week prior to skin flux evaluation.

Skin flux tests were carried out using the general procedure described in J. Pharm. Sci. (1983) 72:968.

The laminate system was die cut out to fit diffusion cells and fentanyl based steady state flux through cadaver skin was determined at 32° C. to be 6.5 mcg/cm$^2$/hr. Perfect sink condition was maintained by using phosphate buffer (pH=6.0) as a receiver fluid. The cumulative amount of fentanyl base released by in vitro dissolution at 25° C. was square root time dependent over 48 hours (correlation coefficient=0.99, slope 139.5 mcg/cm$^2$/hr$^{\frac{1}{2}}$), indicating that diffusion of fentanyl base was under skin control. During 24 hr of skin permeation study 85% of total fentanyl base was delivered and only 15% drug (residual) remained in the composite.

EXAMPLE 2

A three-layer laminated composite for administering fentanyl was prepared in the general manner described in Example 1. It consists of a 75 micron thick reservoir layer of 1.8% fentanyl base, 1.2 to 5% PGML, 2.0% silicone oil and 89.3 to 93.1% of amine resistant polydimethylsiloxane which also act as a pressure-sensitive adhesive sandwiched between a 25 micron thick polyester backing film (3M, 1220) and a 75 micron thick fluorocarbon coated polyester release liner film (3M, 1022) Fentanyl concentration was above saturation (i.e., unit thermodynamic activity). Skin permeation studies were the same as described in Example 1. Fentanyl base steady state flux through cadaver skin was determined at 32° C. to be 7.7 mcg/cm$^2$/hr with approximately 85% of the fentanyl delivered from the composite after 24 hr.

Modifications of the above-described modes for carrying out the invention that are obvious to those of ordinary skill in the field of transdermal drug-delivery devices and related fields are intended to be within the scope of the following claims.

We claim:
1. A solid-state laminated composite for administering fentanyl transdermally comprising:
   (a) a backing layer that is substantially impermeable to fentanyl and defines the face surface of the composite,
   (b) an adhesive fentanyl reservoir layer that defines the basal surface of the composite during use and comprises:
      (i) 1 to 5% by weight fentanyl;
      (ii) 1 to 10% by weight propylene glycol monolaurate (PGML);
      (iii) 85 to 98% by weight of an amine resistant pressure sensitive adhesive polymer having a diffusivity to fentanyl in the range of 10$^{-8}$ to 10$^{-11}$ cm$^2$/sec and a solubility for fentanyl in the range of 1.5 to 5 mg/ml,
   said composite exhibiting a steady state fentanyl skin flux in the range of about 2 to about 10 mcg/cm$^2$/hr and administering at least about 75% of the fentanyl in the composite during approximately the first day of use.

2. The laminated composite of claim 1 wherein the fentanyl comprises 1.7 to 3% be weight of the reservoir layer, the propylene glycol monolaurate comprises 1.5 to 5% by weight of the reservoir layer and the polymer comprises about 90 to 96% by weight of the reservoir layer.

3. The laminated composite of claim 1 wherein the backing layer is occlusive.

4. The laminated composite of claim 3 wherein the polymer is a polydimethylsiloxane.

5. The laminated composite of claim 3 wherein said basal surface has an area of 10 to 40 cm$^2$, the steady state fentanyl flux is in the range of 2 to 10 mcg/cm$^2$/hr and at least about 85% of the fentanyl is administered during approximately the first day of use.

6. The laminated composite of claim 3 including (c) a porous structural layer interposed between the backing layer and the reservoir layer.

7. The laminated composite of claim 6 wherein the porous structural layer is made of a nonwoven fabric.

8. The laminated composite of claim 6 wherein the porous structural layer is adhered to the backing layer by a layer of said amine resistant pressure sensitive adhesive polymer composition.

* * * * *

UNITED STATES PATENT AND TRADEMARK OFFICE
CERTIFICATE OF CORRECTION

PATENT NO. : 5,186,939

DATED : February 16, 1993

INVENTOR(S) : Gary W. Cleary, Samir D. Roy

It is certified that error appears in the above-indentified patent and that said Letters Patent is hereby corrected as shown below:

On the title page, insert the following:

[63] Related U.S. Application Data:

Continuation of Serial No. 700,563, filed May 15, 1991, now abandoned, which is a continuation of Serial No. 588,702, filed Sept. 27, 1990 now abandoned, which is a continuation of Serial No. 425,041, filed October 20, 1989 now abandoned, which is a continuation-in-part of Serial No. 211,377, filed June 24, 1988, now abandoned, which is a continuation-in-part of Serial No. 179,423, filed April 8, 1988, now Patent No. 4,906,463, which is a continuation-in-part of Serial No. 079,801, filed July 30, 1987, now abandoned, which is a continuation-in-part of Serial No. 041,793, filed April 23, 1987, now abandoned Signed and Sealed this Second Day of May, 1995

Attest:

BRUCE LEHMAN

Attesting Officer

Commissioner of Patents and Trademarks